United States Patent [19]

McDonald

[11] Patent Number: 5,630,841
[45] Date of Patent: May 20, 1997

[54] LENS HAPTIC CONTROL

[76] Inventor: Henry H. McDonald, 65 N. Madison, Suite 810, Pasadena, Calif. 91101

[21] Appl. No.: 619,365

[22] Filed: Mar. 21, 1996

[51] Int. Cl.[6] .............................. A61F 2/16; A61B 17/28
[52] U.S. Cl. .......................... 623/6; 606/107; 606/205
[58] Field of Search ................................. 623/6; 606/107, 606/205, 206, 207, 208, 209, 210

[56] References Cited

U.S. PATENT DOCUMENTS

| | | | |
|---|---|---|---|
| 4,759,359 | 7/1988 | Willis et al. | 623/6 X |
| 4,785,810 | 11/1988 | Baccala et al. | 623/6 X |
| 4,813,957 | 3/1989 | McDonald | 623/6 |
| 4,836,201 | 6/1989 | Patton et al. | 623/6 X |
| 4,957,505 | 9/1990 | McDonald | 623/6 |
| 4,959,070 | 9/1990 | McDonald | 623/6 |
| 5,123,905 | 6/1992 | Kelman | 606/107 |
| 5,176,701 | 1/1993 | Dusek et al. | 606/205 X |
| 5,203,790 | 4/1993 | McDonald | 623/6 |
| 5,217,464 | 6/1993 | McDonald | 623/6 X |
| 5,242,450 | 9/1993 | McDonald | 606/107 |
| 5,292,324 | 3/1994 | McDonald | 606/107 |

*Primary Examiner*—Mary Beth Jones
*Attorney, Agent, or Firm*—William W. Haefliger

[57] ABSTRACT

The method of controlling a lens haptic during insertion of an artificial lens into the eye, that includes releasably supporting an end portion of the haptic in a supported position relative to the lens during lens insertion into the eye, such supporting being independent of the lens itself; and permitting the supported end portion of the haptic to progressively release from support as the lens becomes positioned in the eye.

13 Claims, 3 Drawing Sheets

LENS HAPTIC CONTROL

BACKGROUND OF THE INVENTION

This invention relates generally to the control of artificial lens haptic insertion into the eye, and more particularly, to captivation of a lens haptic to enable its full insertion into the eye.

It is typical current practice, when inserting an artificial lens into the eye, to insert the fully projecting leading haptic through the wound and into the eye capsule at the time the lens itself is inserted. The lagging haptic then projects rearwardly through the wound; and it becomes necessary to use auxiliary instrumentation to maneuver the lagging haptic through the wound and into the capsule or "bag".

There is need for method and means to enable full insertion of the lagging haptic at the same time as the lens is moved into the eye, and in such manner that folded lens release by the insertion instrumentation, and subsequent expansion, is not compromised.

SUMMARY OF THE INVENTION

It is a major object of the invention to provide method and means meeting the above need. Basically, the method, in accordance with the invention, for controlling a lens haptic during its insertion into the eye, includes:

a) releasably supporting an end portion of the haptic in a supported position relative to the lens during lens insertion into the eye, such supporting being independent of the lens itself, b) and permitting the supported end portion of the haptic to progressively release from support as the lens becomes positioned in the eye.

Typically, the lens is folded during the insertion into the eye, and such permitting includes allowing unfolding of the lens in the eye in such manner as to assist in haptic release from support.

It is another object to provide insertion instrumentation to engage and transport the lens into the eye, and wherein the releasable supporting of the haptic end portion includes locating the haptic end portion in a recess provided by the instrumentation. The recess is typically shaped in the form of a receptacle; and a guide channel is provided leading toward the receptacle to guide haptic end reception into the receptacle.

A further object is to provide the instrumentation to include a forceps first arm which is elongated, and the recess is provided in that arm. The channel is also provided in that arm, open sidewardly at a side of the arm.

An additional object is to provide the forceps to include a second arm, the lens grasped by and between the arms, and the receptacle is provided at an angled portion of the arm to open toward the channel, to receive the end of the haptic. The lens is typically positioned to locate the haptic in lagging position during insertion. Also, the lagging haptic captivated end is located to tension that haptic, as by resiliently yieldable bending, whereby upon release, the tensioned haptic releases to aid folded lens release from the forceps.

These and other objects and advantages of the invention, as well as the details of an illustrative embodiment, will be more fully understood from the following specification and drawings, in which:

DRAWING DESCRIPTION

DETAILED DESCRIPTION

Figure 1:
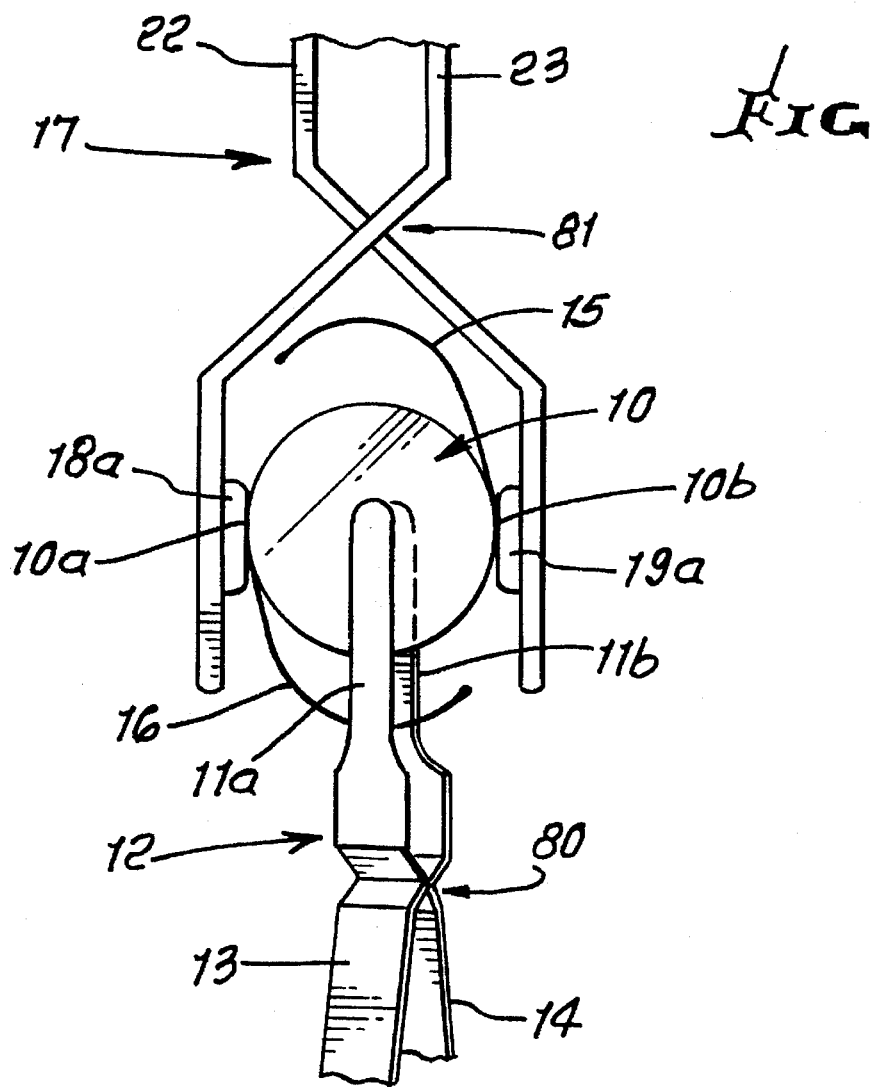
FIG. 1 is an elevation showing a lens holder positioning a held lens between arms of a lens loader.
Figure 4:
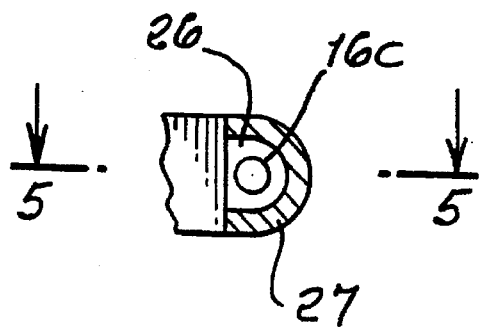
FIG. 4 is an enlarged section taken on lines 4—4 of FIG. 3.

In FIG. 1, an artificial lens 10 is grasped at its opposite sides by arms 11a and 11b of a holder 12. The holder may have arm cross-over construction, as shown at 80, whereby, as handles 13 and 14 are pressed toward one another, the lens is grasped. Note also haptics 15 and 16. A loader instrument 17 is shown receiving the lens, with pads 18a and 19b on arms 18 and 19 grasping opposite edges 10a and 10b of the lens, enabling folding of the lens as the pads are urged toward one another. Note arm cross-over construction at 81, whereby as handles 22 and 23 are urged toward one another, the lens is grasped edgewise and folded. Holder 12 is released when the lens is grasped by the loader.

Figure 2:
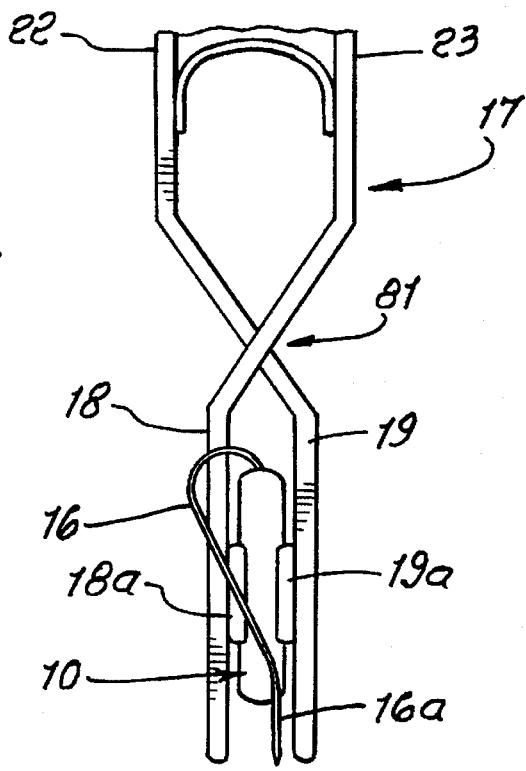
FIG. 2 is a view of a lens loader holding a folded lens, with a haptic oriented in a longitudinal direction.
Figure 3:
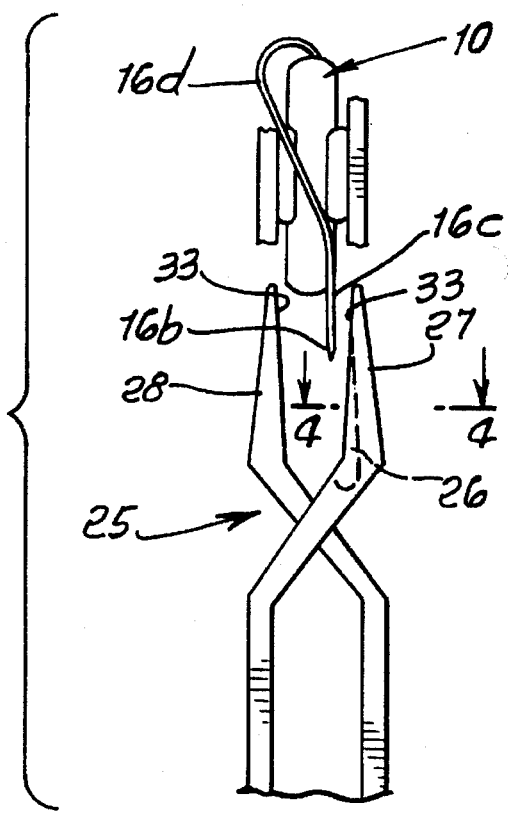
FIG. 3 shows the folded lens being displaced into a folded lens inserted for captivation of the tip of the rear haptic.

FIG. 2 shows the folded lens 10 grasped by the loader arms 18 and 19, and the lens oriented, so that lagging haptic 16 extends as shown, as during loading into an inserter instrument 25. Note the haptic 16 end portion 16a typically oriented by the surgeon to extend longitudinally forwardly for reception into a guide channel 26 in arm 27 of the inserter 25.

Figure 5:
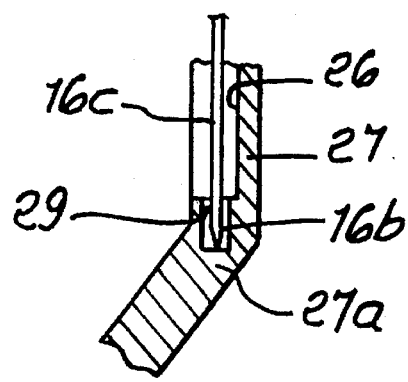
FIG. 5 is an enlarged section taken on lines 5—5 of FIG. 4 showing rear haptic tip captivation.
Figure 6:
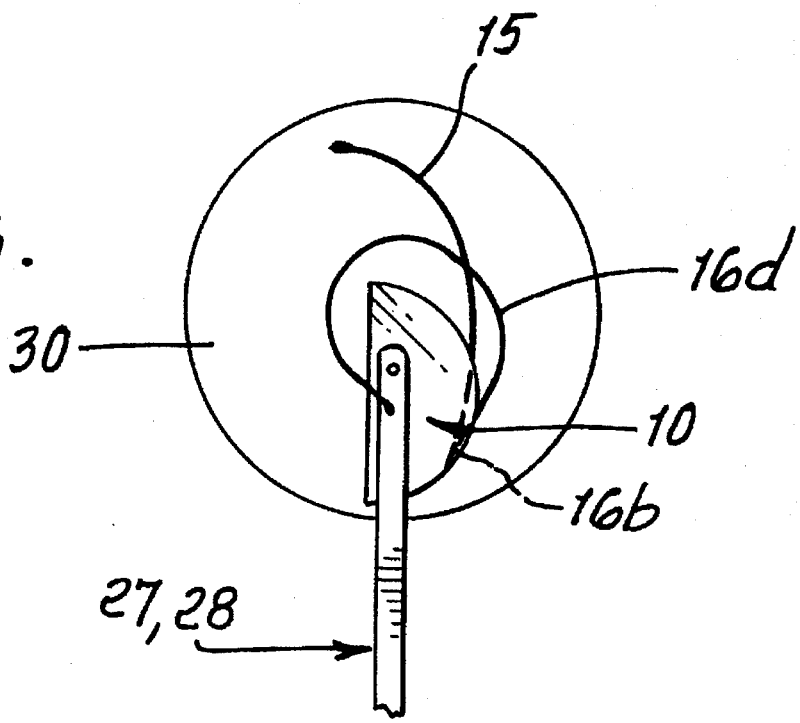
FIG. 6 is a view of the folded lens being inserted by the inserter into the eye capsule, with the captivated rear haptic fully inserted into the eye.

Channel 26 opens sidewardly at the inner side of arm 27, as shown, for progressive reception of the haptic end portion 16a as the folded lens 10 is inserted between inserter arms 27 and 28. Such guided reception of the lagging haptic leads the haptic tip 16a endwise into a recess in the form of a receptacle 29 sunk in arm 27 angled cross-over extent 27a, as shown in FIG. 5. The channel 26 holds the haptic extent 16c nearest the tip in longitudinally oriented constrained condition; however, the remainder 16d of that haptic, outside the channel, bows in a C-shape tensioned condition, urging the haptic end portion or tip into the receptacle during insertion of the lens into the eye, as shown in FIG. 6. That view also shows the leading haptic 15 extending forwardly in the eye, upon insertion.

Accordingly, both haptics are fully received into the lens capsule 30 of the eye, upon insertion by instrumentation 25. See also U.S. Pat. No. 4,813,957, incorporated herein by reference.

Figure 7:
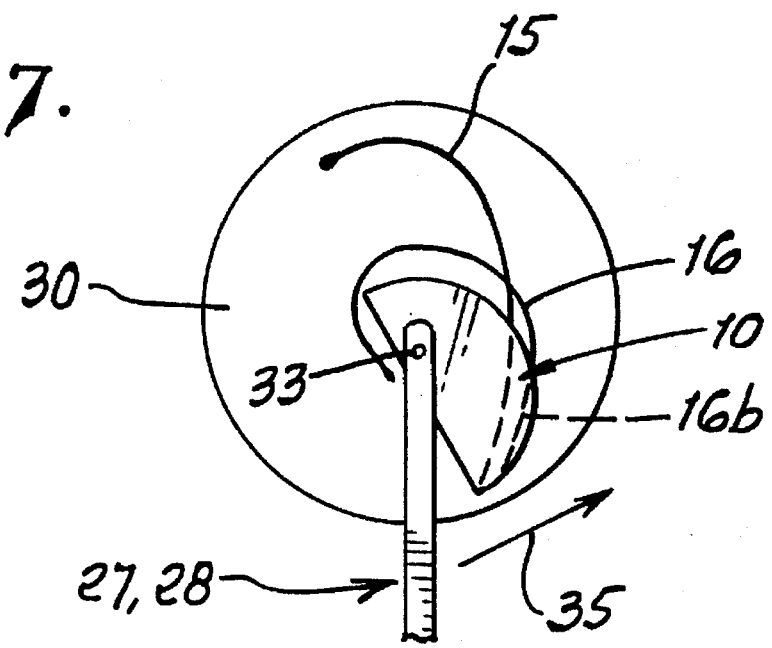
FIG. 7 is a view like FIG. 6 but showing partial release of the folded lens by the inserter, the rear haptic being released from captivation.

FIG. 7 shows the lens 10 becoming unfolded, and pivoting about lens gripping pivots at 33, as the arms 27 and 28 are allowed to spread apart in the eye. As this occurs, the tensioned haptic 16 seeks to release its tensioning, and assists pivoting of the lens in direction 35, relative to arms 27 and 28. During this action, the tip of the haptic 16 easily releases from captivation in receptacle 29, as the haptic slides reversely along channel 26, and out of the channel to become free of the inserter. The latter is then withdrawn from the eye.

In summary, the following are salient factors of tip-trap control of the lagging haptic, not available in other known instruments for intra-ocular, and more significantly, for intra-capsular eye surgery.

1) The tip-trap control is an incomplete tunnel or pit (0.2 by 0.4 mm) in the jaw of a cross action or spring-type forceps, which receives the haptic tip and enables the lagging haptic to assist in the expansion of the folded lens implant into the capsular "bag".

2) Other instruments that grasp a larger area of the haptic, loosely or firmly, have poor control over the lagging haptic and do not permit the natural elasticity of the haptic to go through maneuvers specifically designed for the implantation of the plastic lens. This is the advantage of a strategically confining control rendered by a pit, whereby the haptic cannot push through any opening or slide away in any direction other than that maintained by the control of the tip-trap.

3) Imagine the special spontaneous direction of haptic maneuver permitted by the control of the trip-trap. The endwise compression distorted haptic caught in the trap seeks to spontaneously expand. Permitted expansion of this distorted haptic upon lens implantation causes the haptic to lengthen deeper into the capsule, whereupon it then tip-wise escapes from the tip-trap.

4) The memory of the lagging haptic, with its attachment to the lens implant, which is still held by the forceps, directs the lateral extension of the haptics into the fornixes of the capsule. The haptics then locks and assist in the final expansion of the lens mass, which also becomes anchored permanently in the "bag".

5) Important essentials:

spontaneous simplicity of the tip-trap's control of only the tip of the elastic, lagging haptic permits the average ophthalmologist to participate in one of the most sophisticated small wound surgeries, confortably, confidently and safely.

Avoidance of slashing, exploding release of the haptic is maintained. Use of a cross-action forceps also permits a gradual incremental release of the folded lens implant.

I claim:

1. The method of controlling a lens haptic during insertion of an artificial lens into the eye, that includes
   a) releasably supporting an end portion of the haptic in a supported position relative to the lens during lens insertion into the eye, such supporting being independent of the lens itself,
   b) and permitting the supported end portion of the haptic to progressively release from support as the lens becomes positioned in the eye,
   c) and including tensioning the haptic in said supported position, whereby the tensioned haptic aids release of the lens from support.

2. The method of claim 1 including providing insertion instrumentation to engage and transport the lens into the eye, and wherein said releasable supporting of the haptic end portion includes locating the haptic end portion in a recess provided by said instrumentation.

3. The method of claim 2 including providing said recess in said instrumentation.

4. The method of claim 3 wherein said recess is provided in the form of a receptacle, and a guide channel is provided leading toward the receptacle, to guide haptic end reception into the receptacle.

5. The method of claim 4 wherein said receptacle has a cross dimension of about 0.2 mm, and a depth of about 0.4 mm.

6. The method of claim 5 wherein said channel has a width of about 0.15 mm.

7. The method of claim 1 wherein the lens is positioned to locate said haptic in lagging position during said insertion.

8. The method of controlling a lens haptic during insertion of an artificial lens into the eye, that includes
   a) releasably supporting an end portion of the haptic in a supported position relative to the lens during lens insertion into the eye, such supporting being independent of the lens itself,
   b) and permitting the supported end portion of the haptic to progressively release from support as the lens becomes positioned in the eye,
   c) and wherein the lens is folded during said insertion into the eye, and said permitting includes allowing unfolding of the lens in the eye in such manner as to assist in said release.

9. The method of claim 8 including tensioning the haptic in said supported position, whereby the tensioned haptic aids release of the lens from support.

10. The method of claim 9 wherein the haptic is located as a lagging haptic relative to the direction of lens insertion into the eye.

11. The method of controlling a lens haptic during insertion of an artificial lens into the eye, that includes
    a) releasably supporting an end portion of the haptic in a supported position relative to the lens during lens insertion into the eye, such supporting being independent of the lens itself,
    b) permitting the supported end portion of the haptic to progressively release from support as the lens becomes positioned in the eye,
    c) providing insertion instrumentation to engage and transport the lens into the eye, and wherein said releasable supporting of the haptic end portion includes locating the haptic end portion in a recess provided by said instrumentation,
    d) providing said recess in said instrumentation,
    e) said recess being provided in the form of a receptacle, and a guide channel is provided leading toward the receptacle, to guide haptic end reception into the receptacle,
    f) and wherein said instrumentation includes a forceps first arm which is elongated, and said recess is provided in said arm.

12. The method of claim 11 wherein said channel is also provided in said arm to open sidewardly at a side of the arm.

13. The method of claim 12 wherein said forceps include a second arm, the lens grasped by and between said arms, and said receptacle is provided at an angled portion of said arm to open toward said channel, to receive the end of the haptic.

* * * * *